United States Patent [19]
Ries et al.

[11] Patent Number: 5,549,702
[45] Date of Patent: Aug. 27, 1996

[54] FLEXIBLE ORTHOPAEDIC STEM APPARATUS

[75] Inventors: Michael D. Ries, Cooperstown, N.Y.; Leonard J. Tokish, Jr., Cordova, Tenn.; Thomas W. Fallin, Champaign, Ill.

[73] Assignee: Smith & Nephew Richards Inc., Memphis, Tenn.

[21] Appl. No.: 328,363

[22] Filed: Oct. 25, 1994

[51] Int. Cl.⁶ .................................. A61F 2/34; A61F 2/30
[52] U.S. Cl. .................................. 623/23; 623/18
[58] Field of Search .................... 623/16, 18, 19, 623/20, 22, 23

[56] References Cited

U.S. PATENT DOCUMENTS

| | | | |
|---|---|---|---|
| 4,292,695 | 10/1981 | Koeneman | 3/1.91 |
| 4,743,263 | 5/1988 | Petrtyl et al. | 623/23 |
| 4,784,124 | 11/1988 | Kaltenbrunner et al. | 623/23 |
| 4,808,186 | 2/1989 | Smith | 623/23 |
| 4,840,633 | 6/1989 | Kallabis et al. | 623/23 |
| 4,851,008 | 7/1989 | Johnson | 623/23 |
| 4,904,268 | 2/1990 | Alvarado | 623/23 |
| 4,978,358 | 12/1990 | Bobyn | 623/23 |
| 4,986,834 | 1/1991 | Smith et al. | 623/23 |
| 5,030,234 | 7/1991 | Pappas et al. | 623/23 |

FOREIGN PATENT DOCUMENTS

| | | | |
|---|---|---|---|
| 0019042 | 11/1980 | European Pat. Off. | 623/23 |
| 0077868 | 5/1983 | European Pat. Off. | 623/23 |
| 3913874 | 5/1990 | Germany | 623/23 |
| 2078523 | 9/1984 | United Kingdom . | |
| 2239398 | 7/1991 | United Kingdom . | |

OTHER PUBLICATIONS

"Numerical Optimization Of Hip–Prosthetic Stem Material", J. H. Kuiper and R. Huiskes, pp. 76–84.

*Primary Examiner*—David Isabella
*Attorney, Agent, or Firm*—Pravel, Hewitt, Kimball & Krieger

[57] ABSTRACT

An orthopaedic prosthesis for implantation in a patient's intramedullary canal includes a prosthesis body and a removable prosthesis stem portion that is connectable to the prosthesis body at the lower end portion of the prosthesis body. The stem is formed of an elongated stem member that is preferably conically shaped, having an inner elongated conical core with proximal and distal end portions. A helical portion extends around the core beginning at a position adjacent to the proximal end and terminating at a position adjacent to the distal end. The stem and body can be connectable using a wedge lock or taper-like connection. The prosthesis stem can provide a socket with internal threads for attaching a removal tool thereto.

12 Claims, 9 Drawing Sheets

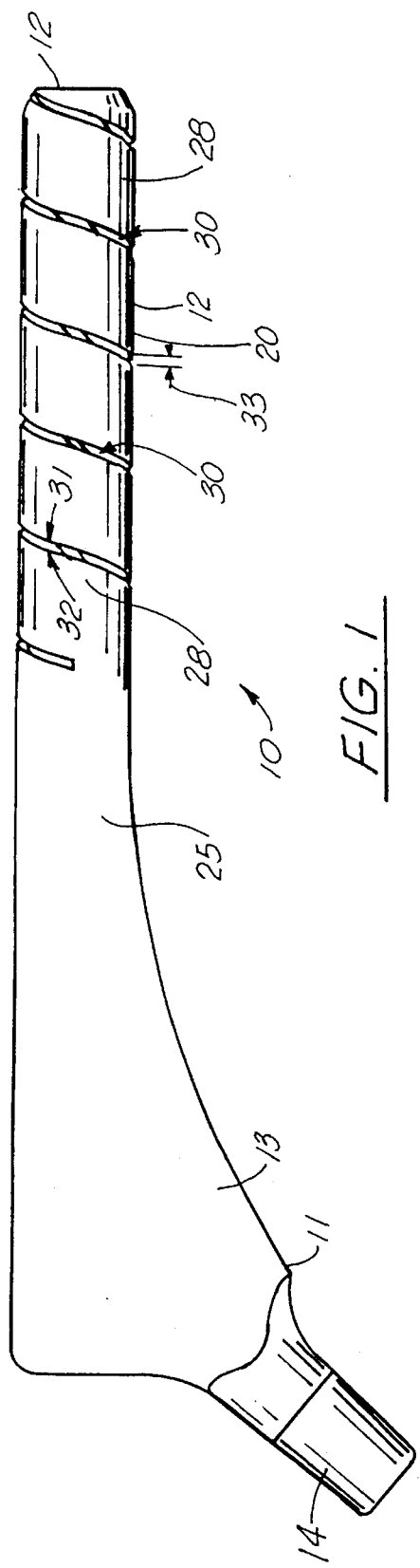
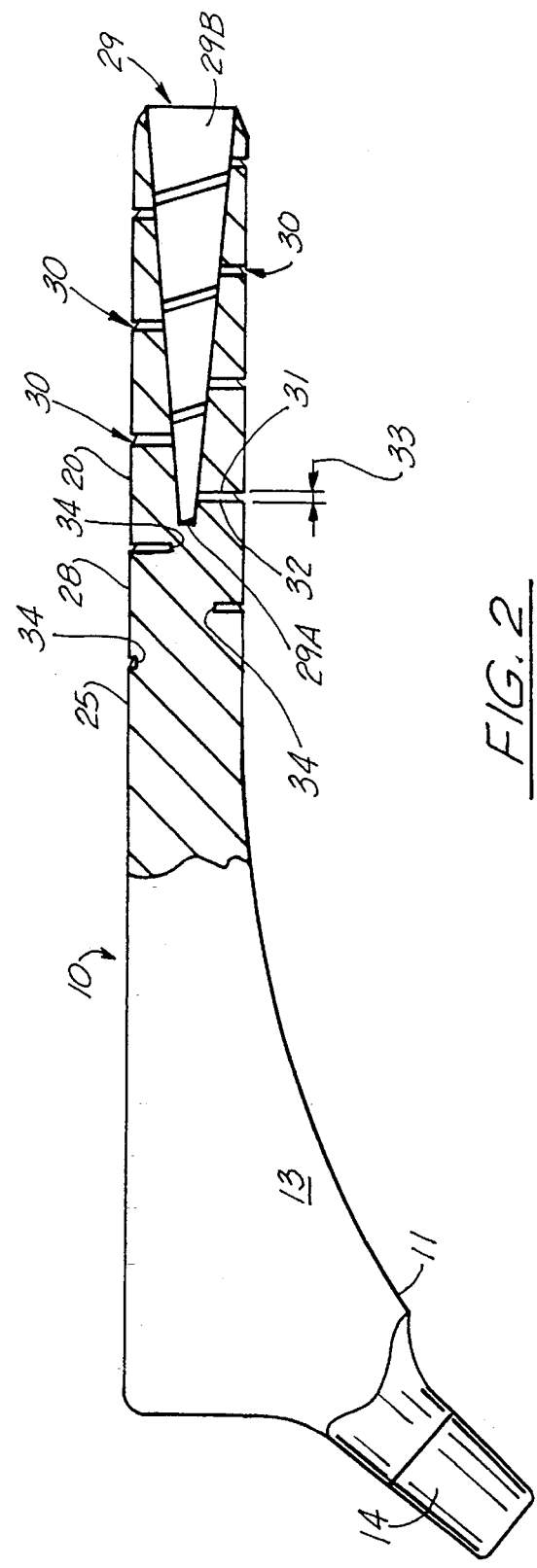

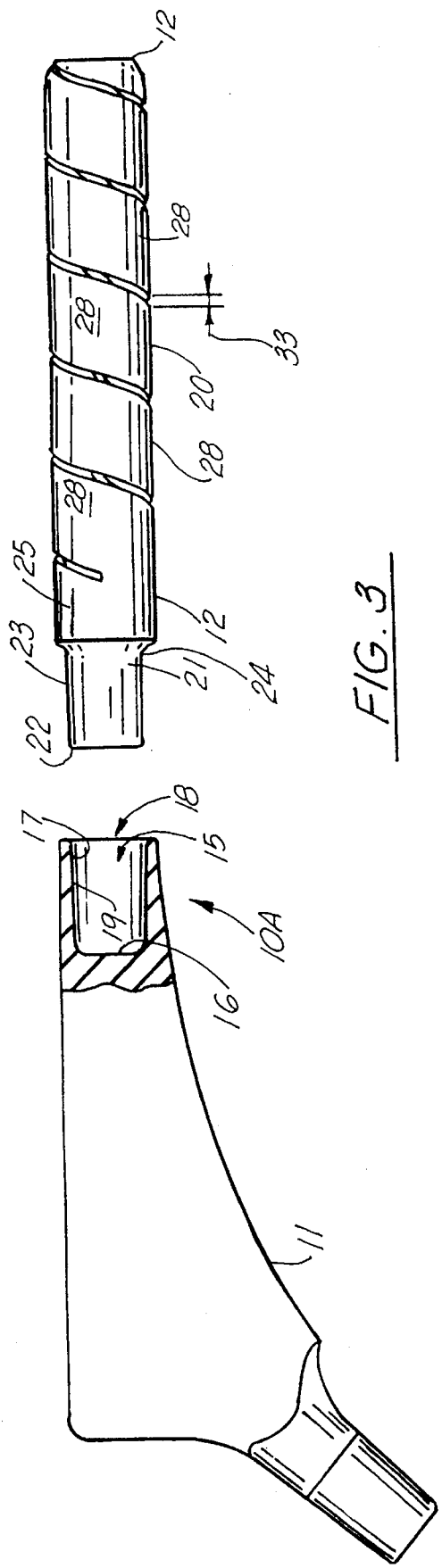
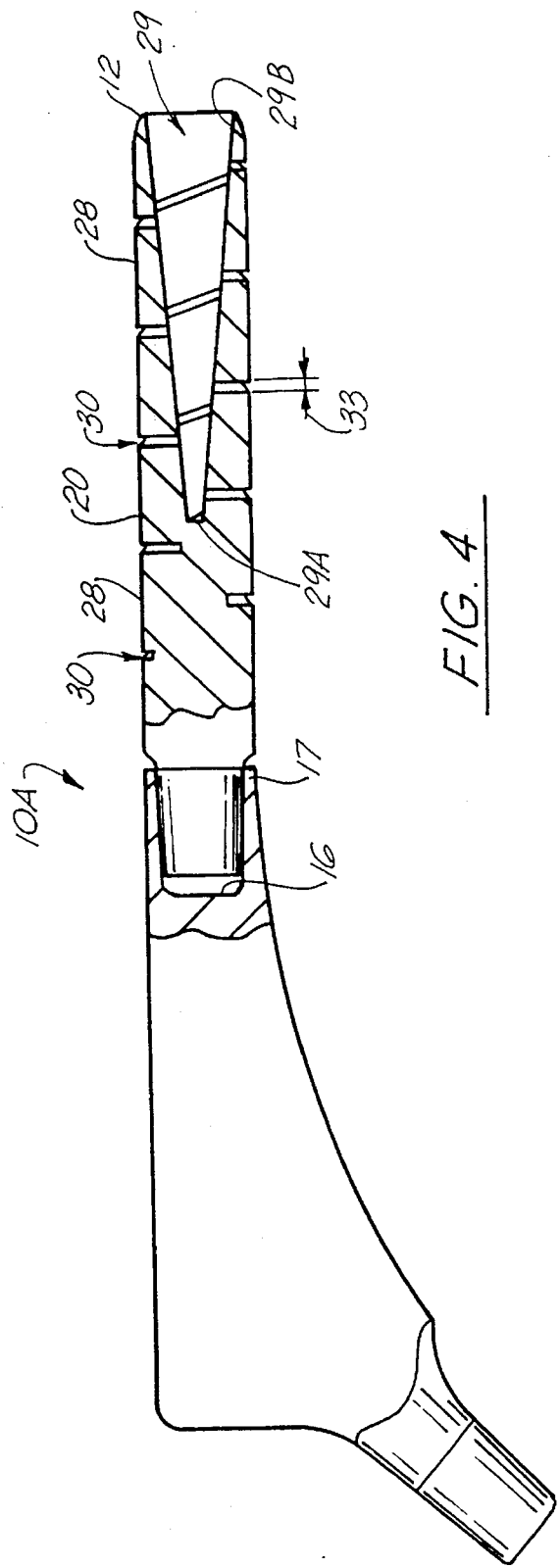
FIG. 3
FIG. 4

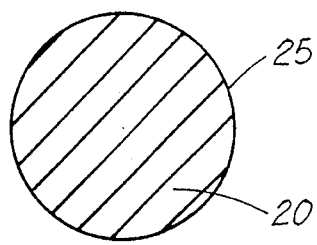
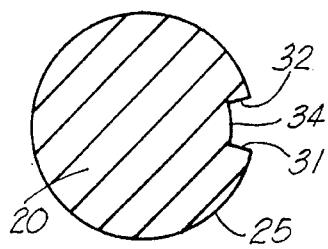
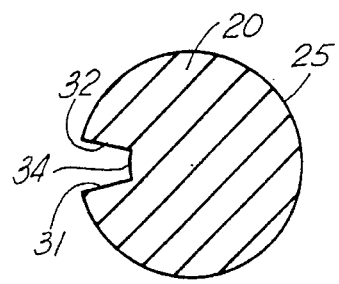
FIG. 6A  FIG. 6B  FIG. 6C
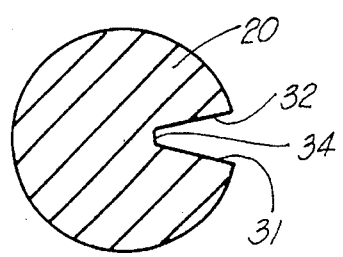
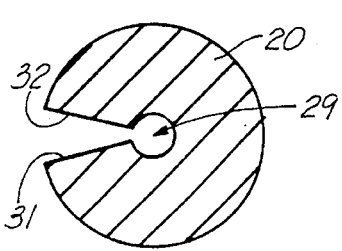
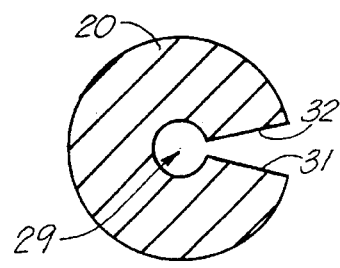
FIG. 6D  FIG. 6E  FIG. 6F
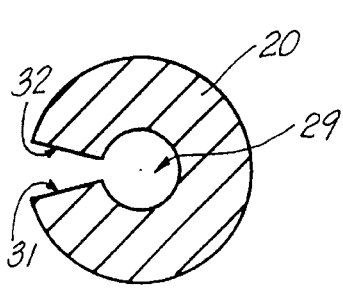
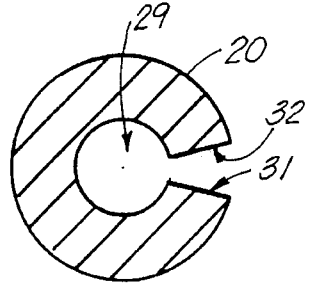
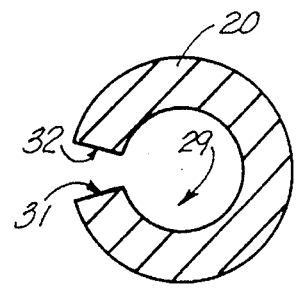
FIG. 6G  FIG. 6H  FIG. 6J
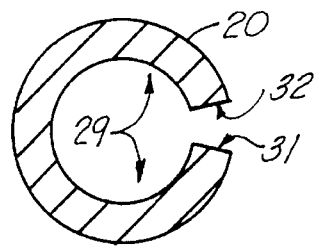
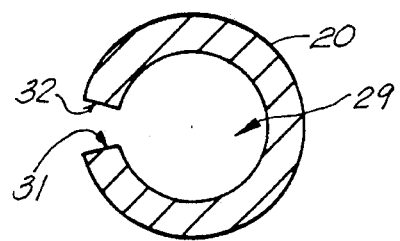
FIG. 6K  FIG. 6L

FLEXIBLE ORTHOPAEDIC STEM APPARATUS

BACKGROUND OF THE INVENTION

1. Field of the Invention

The present invention relates to orthopaedic surgical implants and more particularly relates to an improved orthopaedic stem for use with an implant such as a hip implant or the like. Even more particularly the present invention relates to an improved flexible stem (or shaft) apparatus for use with an orthopaedic implant such as a hip implant wherein the stem includes a helical construct that will ultimately decrease the stiffness and thus improve the flexibility of the shaft portion of an orthopaedic implant.

2. General Background

Surgeons often implant surgical orthopaedic prosthetic devices that include a stem that occupies a portion of the patient's intramedullary canal. Examples include hip stems and tibial prosthetic stems. These prosthetic stems are well documented in the art as part of orthopaedic hip implants, knee implants and the like.

In the evolution of cementless femoral stem components, several problems have emerged. The main concerns are thigh pain and adaptive bone changes of proximal resorption and distal hypertrophy. Thigh pain has been attributed to some degree of instability between the femur and implant. Optimal stability can be achieved with modular components which permit ideal filling of the proximal and distal stem areas. A number of modular systems are now available through different manufacturers.

A growing body of literature supports the concept that flexibility of the stem tip is associated with a lower incidence of thigh pain. One study reports that once proximal bone ingrowth had occurred, severing the distal stem had no effect on the stability of the proximal implant and increased proximal strains. This is consistent with the concept that increasing flexibility at the stem tip combined with a rigid proximal metaphyseal portion will increase proximal load transfer.

One might infer that the stem is not necessary after bone ingrowth has occurred and an optimal stem should have a dissolvable distal stem. However, the distal stem is necessary for stability initially and probably to some extent long term. Applicant has observed late varus migration of certain prior art stems associated with poor filling of the stem tip on the lateral radiograph.

Stability of the stem within the patient's bone is achieved with optimal filling of the proximal and distal femur and may have little dependence on the elastic modulus of the stem material. Furthermore, optimal filling of the proximal and distal femur ensures that load is transferred to the proximal femur in both axial compression and torsion.

An ideal stem should thus consist of a flexible tip and rigid proximal section. This can be made with use of two different materials. A composite tip combined with a titanium proximal implant would achieve this. It also provides an opportunity for modularity, but presents a new interface since two materials contact one another. Designing a durable interface is essential to the feasibility of this implant.

Lack of adequate torsional stability in current stem designs is also a concern. Implants that increase torsional stability by obtaining distal fixation with extensively porous coated implants or distal flutes have been proposed. This is not ideal since torsional load transferred distally is unphysiologic and the proximal bone is stress shielded from torsional loads. A more physiologic stress transfer would ideally load the cortical bone of the calcar in combined axial compression and torsion.

Several patents have issued that relate generally to flexible femoral prostheses. U. K. Patent No. GB 2078523 B, entitled "Hip Joint Prosthesis", provides a hip joint prosthesis for replacement or restoration of the hip joint in a human body. The prosthesis includes a member that is adapted to be attached to the femur and a head portion adapted for cooperation with and movement relative to the acetabulum cavity of the pelvis or of a prosthesis defining such a cavity. The member has an elongated stem extending from the head portion and shaped for insertion into the medullary canal of the femur. The stem has a central axis and includes at least two rigid sections extending parallel to the axis and a resilient elastomeric material disposed between the rigid sections. The rigid sections are spaced laterally from the central axis and from each other.

U.K. Patent GB 2 239 398 A discloses a prosthetic implant having a varying modulus of elasticity. The implant has a shoulder portion and a stem portion comprising struts with a series of structures stacked thereon, the structures including both metal fiber structures and solid metallic structures which are arranged in such a manner that the flexural stiffness varies from one end of the stem to the other. Solid metal disks may alternate with fiber metal mesh disk regions. The relationship between the composite thickness of the mesh stacks and the thicknesses of solid disks determines the flexural stiffness in any particular region. Fiber metal segments of different thicknesses may alternate with solid metal plates. The implant may be particularly a hip prosthesis but may also be a knee, wrist, elbow, or shoulder prosthesis.

U.S. Pat. No. 4,292,695, entitled "Prosthesis Stem", provides an improved stem portion of a joint prosthesis for replacing a damaged or diseased skeletal joint, wherein a series of sections of elastomeric material attached to a rigid material are disposed one on top of the other in a staggered or offset configuration to form the stem. The offset is such that alternate sections of elastomer and rigid material contact selected locations of the bone within the medullary canal to firmly secure the prosthesis therewithin for resisting dislocation particularly during the early stages of postoperative rehabilitation.

U.S. Pat. No. 4,743,263, discloses an adaptable isoelastic hip endoprosthesis that comprises a joint piece connected to a shaft of the endoprosthesis which shaft is to be implanted in the femur, said shaft being composed of at least two spirally twisted elastic rods. Such rods can be of the same cross section, can have a variable cross section, and can have the same or different lengths.

U.S. Pat. No. 4,808,186, issued to T. S. Smith, provides a controlled stiffness elongated implant for use in the hip or other appropriate body joint. In the instance of the hip, a ball member fixed to the femur is rotatably engaged with a cup-shaped socket member fixed to the acetabulum of the pelvic bone. The ball member is mounted on one end of a femoral component which has an elongated stem receivable in the intramedullary canal of the femur. The stem has a longitudinal channel therein which lies generally in the coronal plane when the stem is in the implanted condition. The thickness of the stem laterally of the channel is variable between the proximal and distal ends so as to affect the moment of inertia at any given location along the length of said stem to thereby achieve stem flexibility which substantially correlates to the flexibility of the bone.

An orthopaedic prosthetic device possessing improved composite stem design is disclosed in U.S. Pat. No. 4,978,358. The surgical prosthetic device or implant of the '358 patent comprises a composite structure with an outer metallic component and a separate inner component comprised of the same or a different material. The outer component may be made of commercially pure titanium or a titanium alloy or of a cobalt-based alloy. The inner component may be made of a carbon composite material that may be reinforced or not reinforced with a polymeric material.

A load sharing femoral hip implant is disclosed in the Smith et al. U.S. Pat. No. 4,986,834. The '834 patent discloses a controlled stiffness elongated implant for use in the hip or other appropriate body joint. In the instance of the hip, a ball member fixed to the femur is rotatably engaged with a cup-shaped socket member fixed to the acetabulum of the pelvic bone. The ball member is mounted on one end of a femoral component which has an elongated stem receivable in the intramedullary canal of the femur. The stem has a generally longitudinally directed reduced mid-stem section. The dimension of the reduced mid-stem section is uniform or variable between the proximal and distal ends so as to affect the mass moment of inertia at any given location along the length of said stem to thereby achieve an optimal stem flexibility.

U.S. Pat. No. 5,030,234, entitled "Prosthetic Device With Modular Stem", provides a modular stem type prosthesis which includes a stem and an extension which are connected to one another with a slip fit interconnection that minimizes surface tensile forces in regions of the prosthesis adjacent the interface between the stem and the extension. Engagement between the stem and the extension is provided by deflectable end portions of one component of the prosthesis which are engaged in a mating structures may define an interfitting ridge and groove. Micromotion between the respective parts may be prevented by a screw which may be tapered to achieve a lock fit. The extension may be of any selected length and any selected diameter in accordance with the needs of the patient.

SUMMARY OF THE PRESENT INVENTION

The present invention relates to a surgical orthopaedic implant and more particularly relates to an improved component that is designed to mechanically cooperate with the structural bending of the operated femur, tibia, and/or humerus to more closely reproduce the natural stress distributions seen in the host bone. These goals are accomplished through the controlled variation of properties specific to the distal portion of the implant, including, but not limited to variation in cross sectional area (and thus, mass moment of inertia).

In addition, other design features (to be discussed more fully hereinafter) can be varied to provide additional means of controlling component flexibility, allowing the component to more precisely match the properties of the host bone.

The stem or shaft apparatus includes a helical construct that gradually increases in depth beginning at the proximal end portion of the stem and ending at the distal end portion of the stem and wherein a helical portion surrounds the conical portion so that the combination of the conical portion and helical portion provide predictable flexibility between the proximal and distal end portions of the stem, the helical portion allowing easy removal of the stem from a patient's intramedullary canal if desired.

The preferred embodiment of the present invention includes the use of a stem that incorporates a spring-like helical construct with a constant outside diameter that is incorporated into the distal structure of a femoral, humeral, or tibial implant. The helix begins in the mid-portion of the stem, and proceeds distally to the tip of the stem.

The depth of the helix is varied as it proceeds to the distal tip of the implant, beginning with the a minimal depth at the most proximal portion of the helix, proceeding to a maximum depth at a point between the point of helix origin and the tip of the stem. At the point of maximum helix depth, a point defined by the transition from a solid metal core to an internal conical bore, the helix depth begins to decrease incrementally, arriving once again at a minimum value at the distal tip of the stem.

The preferred embodiment of the present invention includes the use of a modular metal stem extension that incorporates a spring-like helical construct with a constant outside diameter to be used in conjunction with a femoral, tibial, or humeral implant. The depth of the helix is controlled by the incorporation of a tapered cone (inherent to the helical structure) whose cross-section decreases towards the distal end of the sleeve, until, at some point, the cone tapers into and terminates within the helix. Distal to the tapered cone, the helix structure can form a simple helical compression spring structure with a rectangular cross section. The sleeve helix, including the distal tip portion of the helix, is constructed so that the sleeve can be removed from within the medullary canal by unscrewing the construct in much the same way a wood screw is removed from a wood structure.

This concept represents a definite improvement over current art in that it allows the distal portion of a stem to match the variational flexibility and stress distributions of a patient's femur.

The present invention thus provides an improved orthopaedic prosthesis for implantation in a patient's intramedullary canal. The apparatus includes a rigid proximal prosthesis body, and a distal shaft of variable flexibility.

In the preferred embodiment, a helical portion begins at the mid-portion of the apparatus, spiraling distally at a variably increasing depth until it reaches a maximum depth, at which point begins an internal conical bone that ultimately decreases the helix depth as one proceeds distally along the distal portion of the stem, arriving once again at a minimal helix depth at the tip of the stem.

A second embodiment of the present invention incorporates the helical structure described previously (with variable helix depth) into a modular distal stem construct that may be rigidly coupled to a prosthesis body by means of taper connection, threaded connection, or the like. In addition to the benefits obtained with the introduction of modularity, the helical stem extension offers another benefit. The extension helix, including the distal portion of the helix, is constructed such that the stem extension can be removed from within the medullary canal by unthreading the construct in much the same way a standard bolt is removed from a nut.

A number of other embodiments of the present invention can be described that couple some or all of the previously mentioned features with additional structural variations. Thus, a third embodiment may have a helix structure with a constant depth and a constant internal diameter. A fourth embodiment may incorporate the helix structure at a constant depth with a conical bore. A fifth embodiment may eliminate any internal material removal, allowing the helix depth to vary as one proceeds distally to the stem tip, terminating at the tip. Any number of additional variations can be made to the helix angle, helix gap width, helix lead length, etc. For example, two or more helixes (or helical slots) can be provided. These helixes could be both left hand or both right hand wound, in which case the prosthesis could be unscrewed to remove the prosthesis from the intramedullary canal. However, two or more helixes could be provided where one or more is right hand wound, and one or more is left hand wound in which case the prosthesis could not be removed by unscrewing it from the intramedullary canal.

In the preferred embodiment, the helical portion is in the form a regularly spaced continuous helical thread with flanges that are regularly spaced so that the prosthesis can be removed by rotation of the prosthesis so that the prosthesis simply unthreads much in the way that a bolt is unthreaded from a mating nut.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 1 is a side view of the preferred embodiment of the apparatus of the present invention;

FIG. 2 is a partial cross-sectional view of the preferred apparatus of the present invention;

FIG. 3 is a side view of a second embodiment of the apparatus of the present invention that includes a proximally rigid component body and a modular, distally flexible sleeve component;

FIG. 4 is a cross-sectional view of a second embodiment of the present-invention;

FIG. 6A is a cross-sectional view taken along lines A—A of FIG. 5;

FIG. 6B is a cross-sectional view taken along lines B—B of FIG. 5;

FIG. 6C is a cross-sectional view taken along lines C—C of FIG. 5;

FIG. 6D is a cross-sectional view taken along lines D—D of FIG. 5;

FIG. 6E is a cross-sectional view taken along lines E—E of FIG. 5;

FIG. 6F is a cross-sectional view taken along lines F—F of FIG. 5;

FIG. 6G is a cross-sectional view taken along lines G—G of FIG. 5;

FIG. 6H is a cross-sectional view taken along lines H—H of FIG. 5;

FIG. 6J is a cross-sectional view taken along lines J—J of FIG. 5;

FIG. 6K is a cross-sectional view taken along lines K—K of FIG. 5;

FIG. 6L is a cross-sectional view taken along lines L—L of FIG. 5;

DETAILED DESCRIPTION OF THE PREFERRED EMBODIMENT

Figure 5:
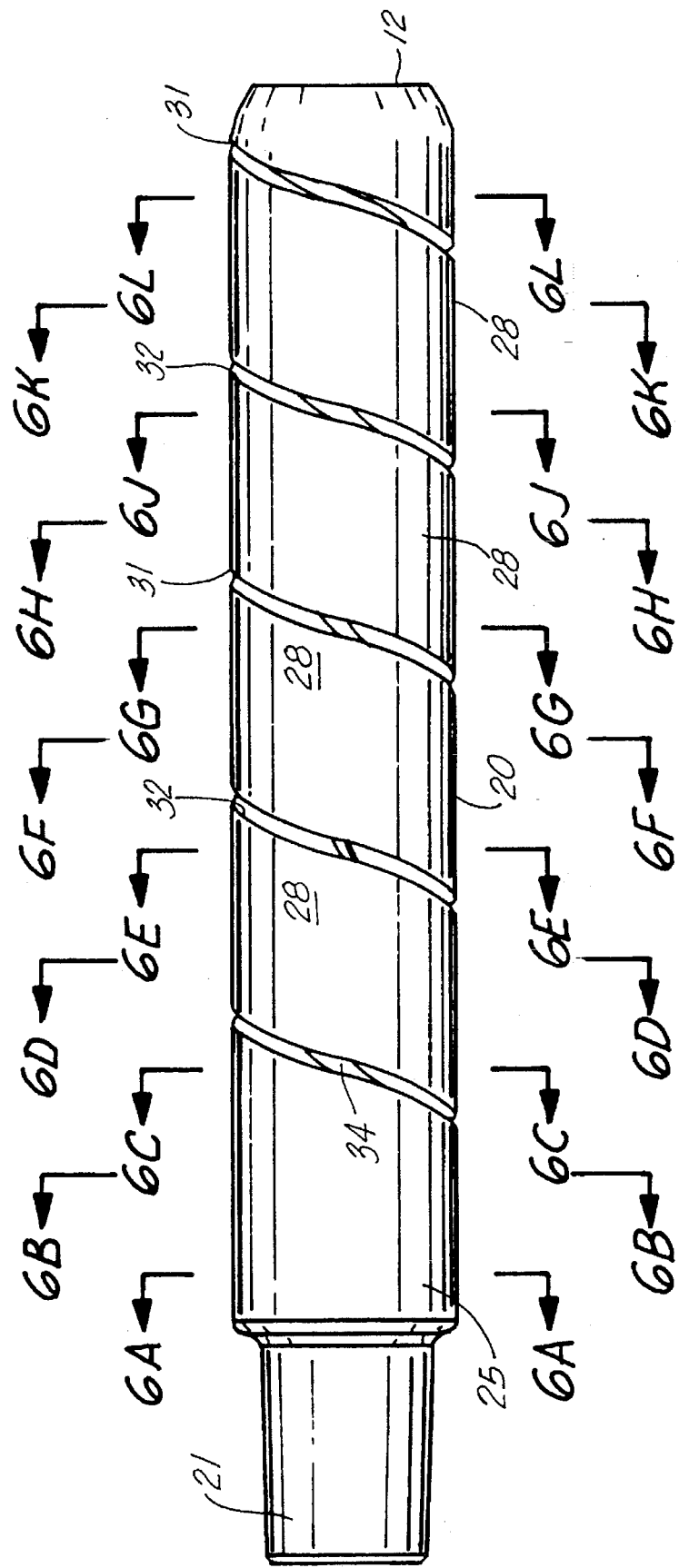
FIG. 5 is a partial side view of a second embodiment of the present invention that illustrates a modular, distally flexible sleeve with cross sections shown.

FIGS. 1 and 2 illustrate the preferred embodiment of the apparatus of the present invention designated generally by the numeral 10. In FIGS. 1 and 2, a hip orthopaedic implant is shown. However, it should be understood that the present invention has utility with respect to other orthopaedic implants such as knee implants, shoulder implants and the like. In FIGS. 1 and 2, the implant 10 has an upper proximal end portion 11 and a lower distal end portion 12. The upper end portion of prothesis 10 is in the form of a hip implant having a thickened body portion 13.

In FIGS. 1–2, implant 10 includes a neck region 14 for accepting a ball that registers with the patient's acetabulum. In both embodiments of FIGS. 1–2 and 3–5, a continuous helical portion 28 extends from cylindrical section 25 to distal end 12. Helical portion 28 surrounds inner tapered bore portion 29. Tapered bore portion 29 begins adjacent cylindrical section 25 at smaller diameter circular end portion 29A and extends to larger diameter portion 29B at distal end 12. In the embodiment of FIGS. 3–4, designated by the numeral 10A, the prosthesis has proximal 11 and distal 12 end portions. Proximal end portion 11 has a lower tapered socket 15, with a smaller diameter section 16 and a larger diameter section 17 that communicates with open end 18. Socket 15 side wall 19 is preferably tapered and shaped to receive section 21. Socket 15 forms a wedge lock or taper lock fit with conical section 21 of stem 20. Conical section 21 includes a smaller diameter end portion 22 and a larger diameter end portion 23.

Annular shoulder 24 is curved to form a transition between the conical surface 21 and the generally cylindrically shaped surface 25 shown in the drawings.

In both embodiments of FIGS. 1–2 and 3–5, a continuous helical portion 28 extends from cylindrical section 25 to distal end 12. Helical portion 28 surrounds inner tapered bore portion 29. Tapered bore portion 29 begins adjacent cylindrical section 25 at smaller diameter circular end portion 29A and extends to larger diameter portion 29B at distal end 12. Helical portion 28 and conical portion 29 are preferably integrally connected and can be of a metallic or composite construction, for example.

A continuous spiralling recess 30 defines a space that is also helical, the space 30 tracking the helical portion 28. The combination of helical portion 28 tapered conical bore section 29 provides a means of varying the flexibility of stem 20 between end portion 22 and distal end 12. For example, the helical portion 28 could be made thicker between transverse faces 31, 32, that thickness dimension being designated by the numeral 33 in FIGS. 1–4. Further, the conical bore section can be varied in diameter with a smaller diameter at 29A and a larger diameter at 29B.

FIGS. 6A to 6L illustrate an example of the amount of cross-section (and thus mass moment of inertia) variation that can be introduced by the embodiment illustrated in FIGS. 3–5.

Figure 7:
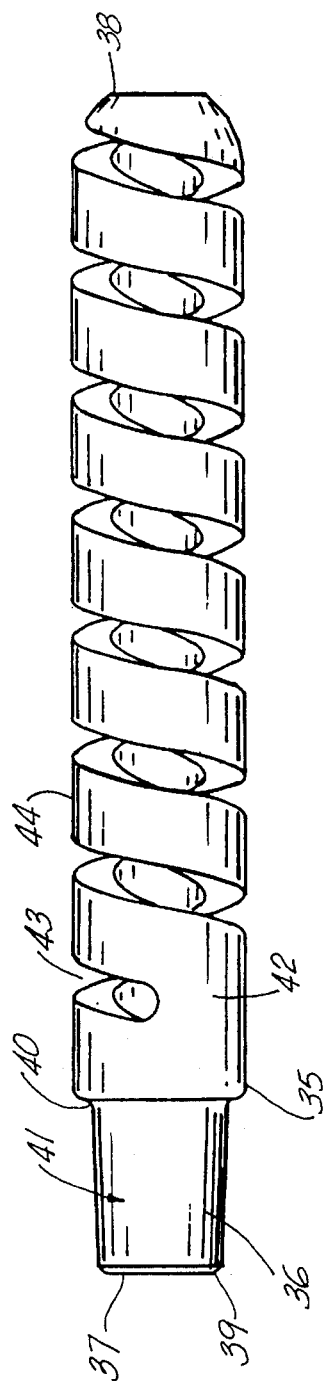
FIG. 7 is a side view of a third embodiment of the present invention, which illustrates the helical construct at a constant depth, coupled with a constant internal diameter.
Figure 8:
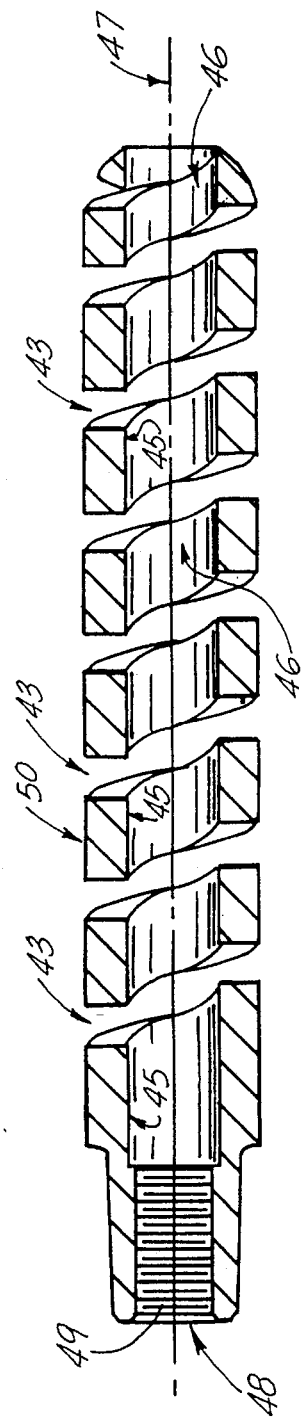
FIG. 8 is a cross-sectional view of a third embodiment of the present invention.

FIGS. 7 and 8 show an alternate stem 35 that can be used with the thickened body section 13 of FIGS. 3–5. Stem 35 includes a proximal end 36 having a generally circular smaller diameter portion 37 and a generally circular larger diameter portion 40. This produces a frustroconically-shaped portion 41 that extends between the smaller diameter at 7 and the larger diameter at 40. Frustroconical portion 41 can connect with a wedge-lock connection to socket 15 (FIG. 3). Stem 35 includes a generally cylindrically shaped portion 42 and a continuous spiralling slot 43 that extends from cylindrical section 42 to distal end 38. The spiralling slot 43 defines a helical construct 44 that has an inner surface 45 and an outer surface 50. The inner surface 45 defines a cylindrically-shaped bore 46 that extends the length of the stem 35, having a central longitudinal bore axis 47. The proximal end 36 includes a threaded section 49 that extends between the bore 46 and open end 48. The bore 46 provides internal threads 49 that accommodate a removal tool should stem 35 be desirably removed from the patient's intramedullary canal after being implanted.

Figure 9:
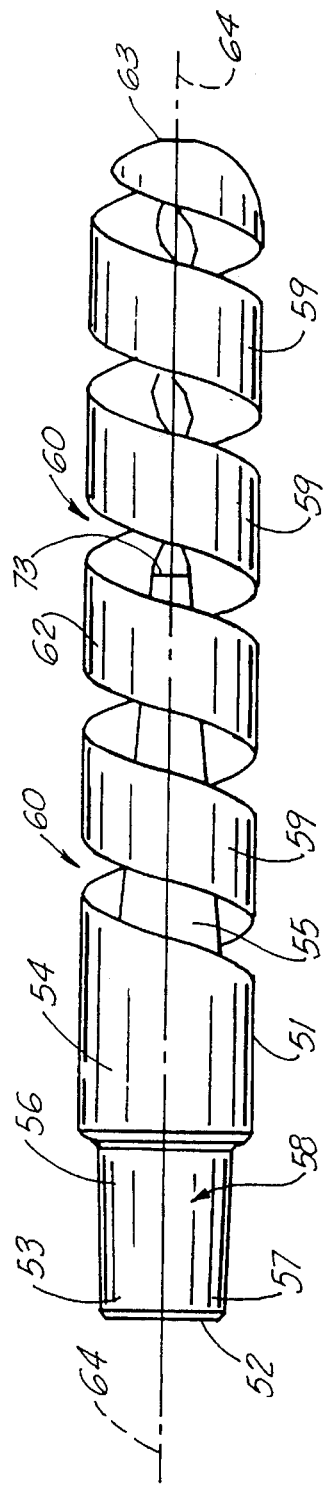
FIG. 9 is a side view of a fourth embodiment of the apparatus of the present invention, which illustrates a helical construct with a variable depth coupled with a constant internal diameter.
Figure 10:
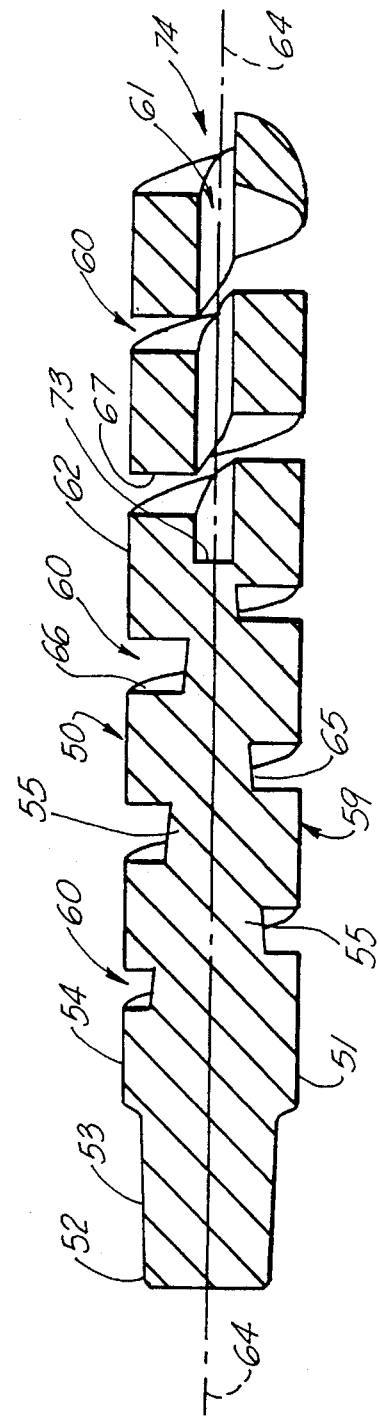
FIG. 10 is a cross-sectional view of a fourth embodiment of the apparatus of the present invention.

In the embodiment of FIGS. 9 and 10, a stem 51 is provided having a proximal end portion 52 and distal end portion 63. The stem proximal end portion 52 includes a frustroconical section 53 that connects to a generally cylindrically-shaped section 54. Frustroconical section 53 can be connected to socket 15 (FIG. 3) using a wedge-lock or taper lock connection. An elongated tapered core 55 extends from the cylindrical section 54 in a direction toward the distal end portion. The frustroconical section 53 includes larger diameter section 56 and smaller diameter section 57, providing a generally conically or frustroconically-shaped outer surface 58.

Stem outer surface 59 is generally cylindrically shaped at cylindrically-shaped section 54 but is in interrupted with spiralling slot 60 that initiates at cylindrical section 54 and proceeds to the distal tip end 63. The spiralling slot 60 defines a helical construct 62 at bore 61. A generally cylindrically-shaped bore 61 extends from closed end portion 73 and communicating with the open end 74 of bore 61. Stem 51 and bore 61 share a common central longitudinal axis 64. A pair of spiralling shoulders 66, 67 and spiralling longitudinally extending surface 65 define the boundaries of spiralling slot 60.

Figure 11:
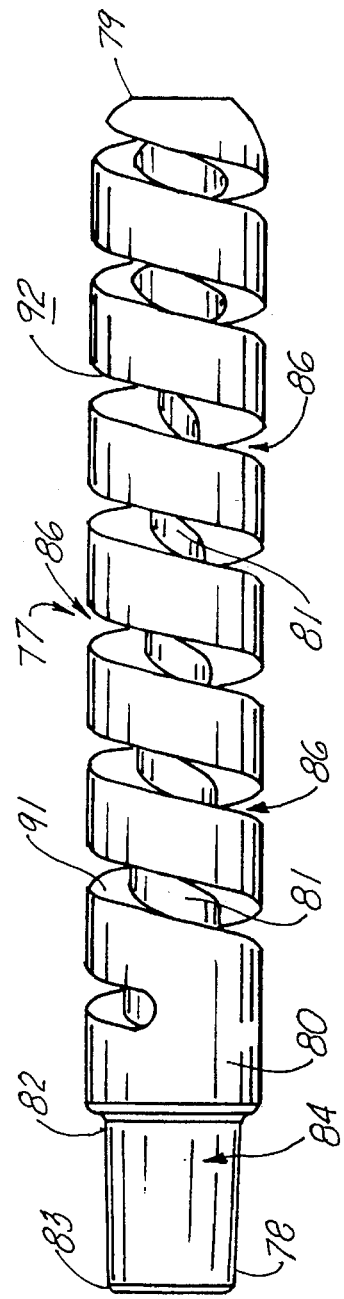
FIG. 11 is is a side view of a fifth embodiment of the apparatus of the present invention, which illustrates a helical construct with a variable depth coupled with a constant internal diameter, illustrating the variation that can be designed into the apparatus when compared to the fourth embodiment.
Figure 12:
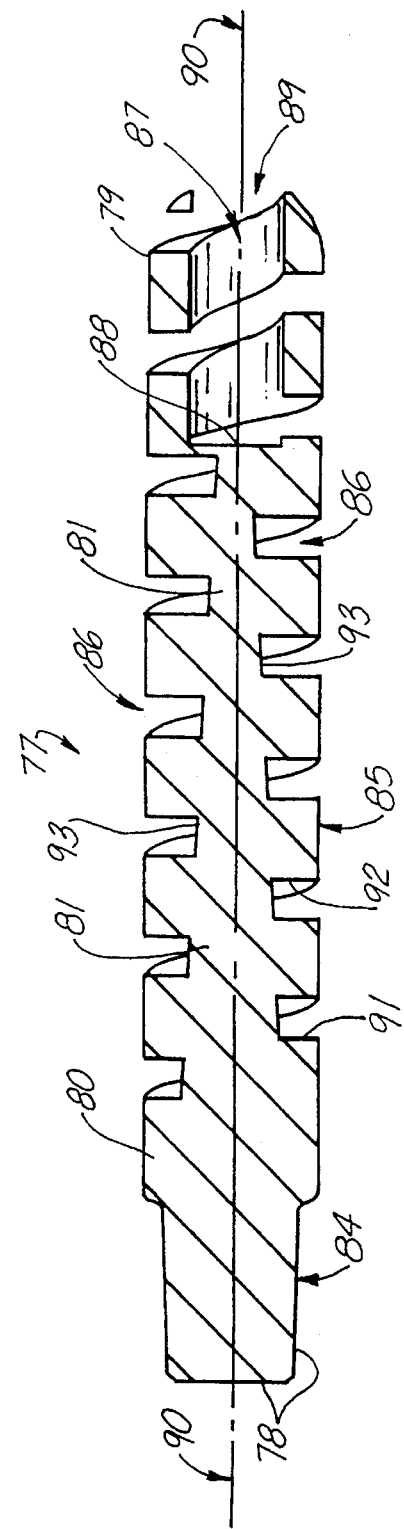
FIG. 12 is a cross-sectional view of the fifth embodiment of the apparatus of the present invention.

In the embodiment of FIGS. 11 and 12, a stem 77 is provided having a proximal end portion 78 and distal end portion 79. The stem proximal end portion 78 includes a frustroconical section 84 that connects to a generally cylindrically-shaped section 80. Frustroconical section 84 can be connected to socket 15 (FIG. 3) using a wedge-lock or taper lock connection. An elongated tapered core 81 extends from the cylindrical section 80 in a direction toward the distal end portion. The frustroconical section 84 includes larger diameter section 82 and smaller diameter section 83, providing a generally conically or frustroconically-shaped outer surface.

Stem outer surface 85 is generally cylindrically shaped at cylindrically-shaped section 80 but is in interrupted with spiralling slot 86 that initiates at cylindrical section 80 and proceeds to the distal tip end 79. An enlarged, generally cylindrically-shaped bore 87 extends from closed end portion 88 and communicating with the open end 89. Stem 77 and bore 87 share a common central longitudinal axis 90. A pair of spiralling shoulders 91, 92 and spiralling longitudinally extending surface 93 define the boundaries of spiralling slot 86.

Figure 13:
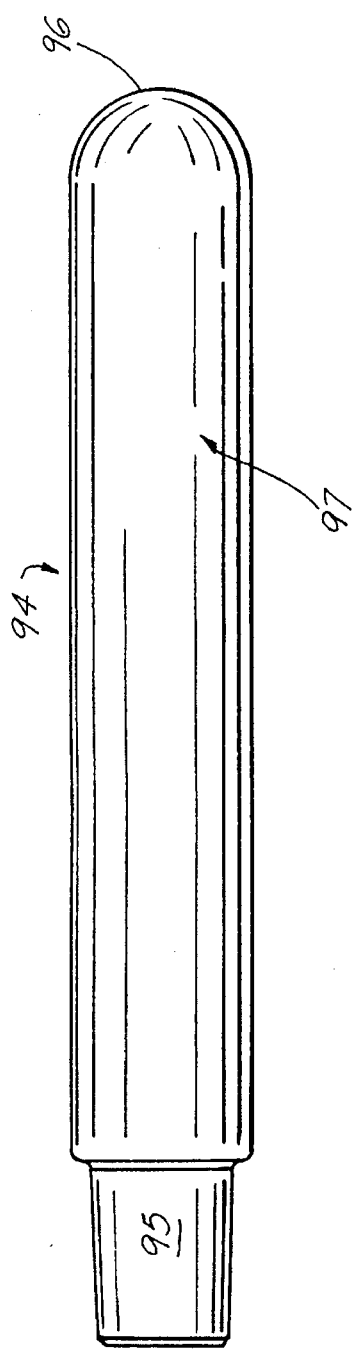
FIG. 13 is a side view of a unmodified stem portion.
Figure 14:
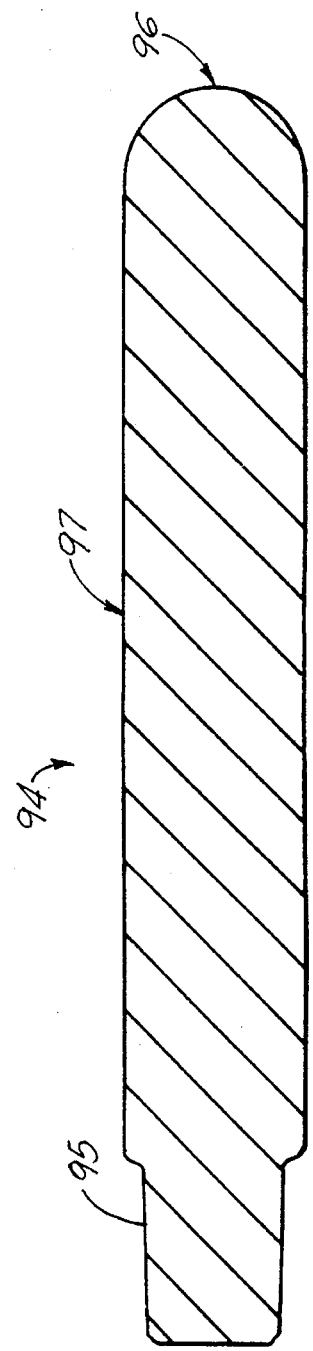
FIG. 14 is a cross-section view of an unmodified stem portion.
Figure 15:
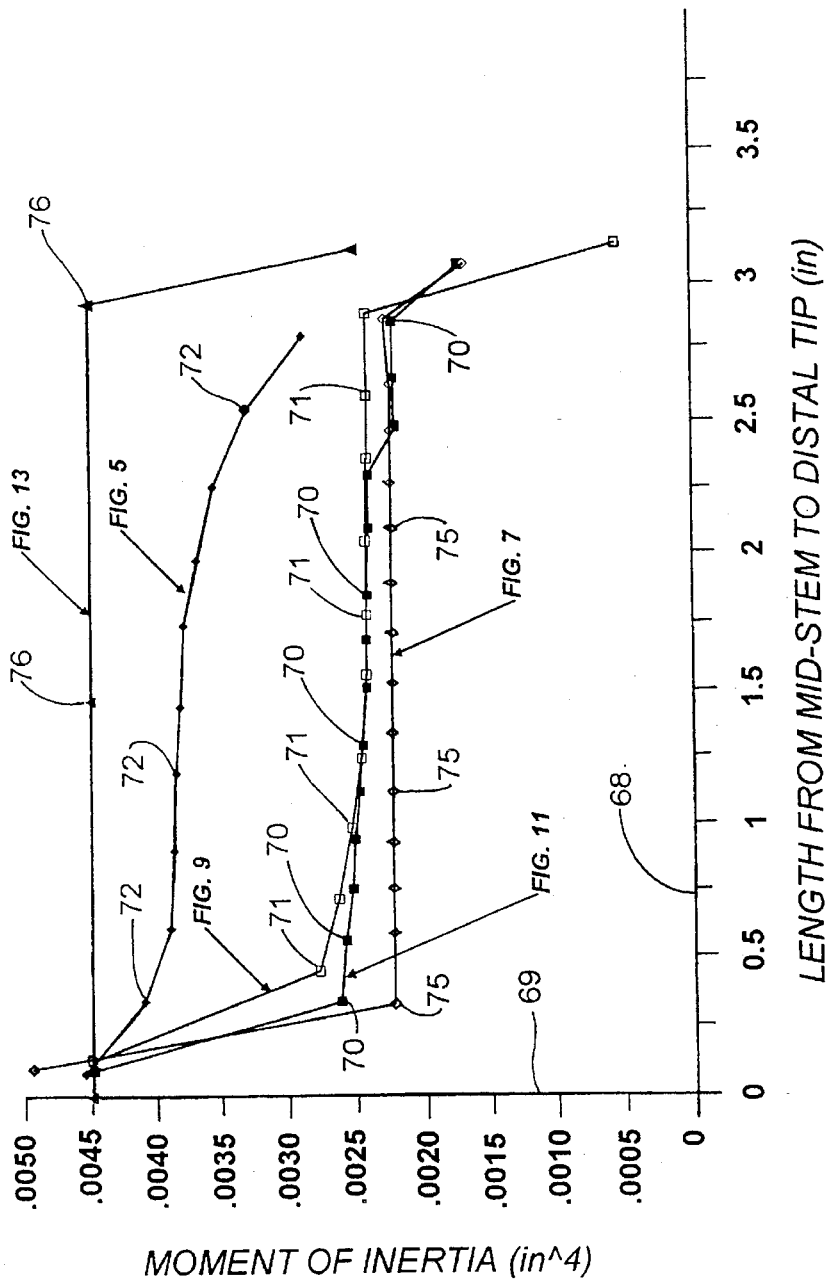
FIG. 15 is a graphical illustration of the relationship between the distance (from mid-stem to distal tip) along the prosthesis and the moment of inertia of the prosthesis at the given distance for the four different embodiments of the present invention shown in FIGS. 5, 7, 9, and 11, as well as for the unmodified prosthesis shown in FIG. 13.

In FIGS. 13–14, a prior art type stem is shown, designated by the numeral 94. the stem 94 has a frustroconical proximal end 95, a hemispherical end 96 and a cylindrical outer surface 97. In FIG. 15, there is seen a graphical representation of the moment of inertia, considering a stem that has a given distance from mid stem to distal tip. In FIG. 15, the x-axis 68 represents the distance from mid stem to distal tip in inches and the moment of inertia is indicated at the y-axis 69. The black squares 70 are data for the embodiment of FIG. 11. The black diamonds 72 are data for the embodiment of FIG. 5. The white squares 71 are data for the embodiment of FIG. 9. The white diamonds 75 are data for the embodiment of FIG. 7. The black triangles 76 are data for the embodiment of FIG. 13, which represents an unmodified cylindrical stem portion.

The following table lists the part numbers and part descriptions as used herein and in the drawings attached hereto.

| PARTS LIST | |
|---|---|
| Part Number | Description |
| 10 | orthopaedic prosthesis |
| 10A | orthopaedic prosthesis |
| 11 | proximal end |
| 12 | distal end |
| 13 | thickened section |
| 14 | neck |
| 15 | socket |
| 16 | smaller diameter section |
| 17 | larger diameter section |
| 18 | open end |
| 19 | side wall |
| 20 | stem |
| 21 | conical section |
| 22 | smaller diameter end portion |
| 23 | larger diameter end portion |
| 24 | shoulder |
| 25 | cylindrical surface |
| 28 | helical portion |
| 29 | tapered bore portion |
| 29A | smaller diameter section |
| 29B | larger diameter section |
| 30 | spiralling recess |
| 31 | transverse face |
| 32 | transverse face |
| 33 | thickness |
| 34 | spiralling surface |
| 35 | stem |
| 36 | proximal end portion |
| 37 | smaller diameter section |
| 38 | distal end portion |

-continued

PARTS LIST

| Part Number | Description |
| --- | --- |
| 40 | larger diameter section |
| 41 | frustroconical section |
| 42 | cylindrically shaped portion |
| 43 | spiralling slot |
| 44 | helical construct |
| 45 | inner surface |
| 46 | bore |
| 47 | central longitudinal axis |
| 48 | open bore |
| 49 | internal threads |
| 50 | outer surface |
| 51 | stem |
| 52 | proximal end portion |
| 53 | frustroconical section |
| 54 | cylindrical section |
| 55 | tapered core |
| 56 | larger diameter section |
| 57 | smaller diameter section |
| 58 | conical outer surface |
| 59 | stem outer surface |
| 60 | spiralling slot |
| 61 | cylindrical bore |
| 62 | helical construct |
| 63 | distal end |
| 64 | central longitudinal axis |
| 65 | spiralling surface |
| 66 | spiralling shoulder |
| 67 | spiralling shoulder |
| 68 | x - axis |
| 69 | y - axis |
| 70 | black square |
| 71 | white square |
| 72 | black diamond |
| 73 | closed end |
| 74 | open end |
| 75 | white diamond |
| 76 | black triangle |
| 77 | stem |
| 78 | proximal end portion |
| 79 | distal end portion |
| 80 | cylindrical section |
| 81 | tapered core |
| 82 | larger diameter section |
| 83 | smaller diameter section |
| 84 | frustroconical section |
| 85 | stem outer surface |
| 86 | spiralling slot |
| 87 | cylindrical bore |
| 88 | closed end portion |
| 89 | open end |
| 90 | central longitudinal axis |
| 91 | spiralling shoulder |
| 92 | spiralling shoulder |
| 93 | spiralling surface |
| 94 | stem |
| 95 | frustroconical proximal end |
| 96 | hemispherical end 96 |
| 97 | cylindrical outer surface |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An orthopaedic prosthesis for implantation in a patient's intramedullary canal comprising
   a) a prosthesis body that includes a generally rigid proximal portion sized and shaped to fit the intramedullary canal of a patient's bone;
   b) prosthesis stem and mid portions on the prosthesis body, the stem portion including a lower elongated stem member with a an outer surface and distal end;
   c) the lower stem member providing a helical groove and a cooperating hollowed tapered core portion that enable the distal end to flex; and
   d) said helical groove extending between the outer surface of the stem and the hollowed core along a majority of the length of the hollowed core.

2. The prosthesis of claim 1 wherein the helical groove begins in the mid-portion of the prosthesis and proceeds distally to the tip of the stem.

3. The prosthesis of claim 2 wherein the depth of the helical groove is varied radially in thickness as it proceeds distally, beginning with a minimum depth at the most proximal portion of the helix.

4. The prosthesis of claim 1 wherein the core comprises a conically tapered bore with minimum and maximum diameter portion, said bore extending to the distal tip of the prosthesis, said bore terminating at the tip of the stem at said maximum inside diameter.

5. The prosthesis of claim 1 wherein the helical groove begins in the mid-portion of the prosthesis body and proceeds distally to the distal tip of the stem.

6. An orthopaedic prosthesis for implantation in a patient's intramedullary canal comprising:
   a) a prosthesis body that includes a generally rigid proximal portion sized and shaped to fit the intramedullary canal of a patient's bone:
   b) prosthesis stem and mid portions on the prosthesis body, the stem portion including a lower elongated stem member with a distal end;
   c) the lower mid and stem member portions providing a helical groove and a cooperating core portion that enables the distal end to flex;
   d) wherein the depth of the helical groove is varied in thickness radially as it proceeds distally, beginning with a minimum depth at the most proximal portion of the helix proceeding to a maximum depth at a point between the point of helix origin and the tip of the stem, where the internal core terminates.

7. The protheses of claim 1 wherein the core is conically shaped and tapered along the length thereof.

8. The prosthesis of claim 7 wherein the taper is a uniform taper beginning at a first diameter and tapering uniformally to a second diameter that is smaller that the first diameter.

9. The prosthesis of claim 1 wherein the body includes a neck portion having means thereon for attaching a prosthetic acetabular ball portion thereto.

10. The prosthesis of claim 1 wherein the helical groove includes a pair of generally parallel transverse face portions.

11. An orthopaedic hip prosthesis for implantation in a patient's femoral intramedullary canal comprising
   a) a prosthesis body having a larger thickened central portion, an upper neck portion and a lower, smaller portion;
   b) a prosthesis stem portion that extends from the smaller portion, and including an elongated stem member having an outer surface, proximal and distal ends, and an internal elongated hollow bore;
   c) a helical groove portion that extends around the stem beginning at a position adjacent to the proximal end of the stem and terminating at a position adjacent to the distal end of the stem; and
   d) wherein the bore is conically shaped, and the groove extends between the bore and the outer surface of the stem.

12. An orthopaedic hip prosthesis for implantation in a patient's femoral intramedullary canal comprising
   a) a prosthesis body having a larger thickened central portion, an upper neck portion and a lower, smaller portion;
   b) a prosthesis stem portion that extends from the smaller portion, and including an elongated stem member having an outer surface, proximal and distal ends, and an internal elongated hollow bore;
   c) a helical groove portion that extends around the stem beginning at a position adjacent to the proximal end of the stem and terminating at a position adjacent to the distal end of the stem; and
   d) wherein the groove continuously extends between the stem outer surface and the hollow bore.

* * * * *